United States Patent [19]

Mueller

[11] 4,168,775

[45] Sep. 25, 1979

[54] IDLER SPROCKETS FOR SAMPLE CHANGER TRACKS

[75] Inventor: Anthony A. Mueller, Florence, Ky.

[73] Assignee: Actus, Inc., Florence, Ky.

[21] Appl. No.: 814,986

[22] Filed: Jul. 12, 1977

[51] Int. Cl.$^2$ .............................................. B65G 35/08
[52] U.S. Cl. .................................... 198/795; 198/472; 250/328
[58] Field of Search ............... 198/339, 472, 580, 648, 198/655, 656, 720, 723, 795; 214/310; 250/328, 336, 338; 73/421 R, 423 A; 266/180

[56] References Cited

U.S. PATENT DOCUMENTS

| 2,424,055 | 7/1947 | Rousseau | 198/795 |
| 3,201,102 | 8/1965 | Stieler et al. | 198/795 |
| 3,270,202 | 8/1966 | Long et al. | 250/328 |
| 3,553,454 | 1/1971 | Olson et al. | 250/328 |
| 4,001,584 | 1/1977 | Mueller et al. | 250/328 |
| 4,024,395 | 5/1977 | Mueller et al. | 250/328 |

Primary Examiner—Joseph E. Valenza
Attorney, Agent, or Firm—Fleit & Jacobson

[57] ABSTRACT

A toothed sprocket wheel provides an idler for driving test tube holders into and out of sharp turns which occur in the track of an automatic sample changer employed in radiopharmaceuticals. The sprocket is provided with a selected number of well-defined teeth and is rotatably mounted at the center of a relatively sharp turn so as to transfer the linear motion from the test tube holder at its point of entry into the turn to the test tube holder at the point of exit from the turn. Also disclosed is a tensioner or positioner in a substantially linear alignment of the test tube holders such that, upon varying the degree of insertion of the sprocket teeth between successive test tube holders, the relative spacing between successive test tube holders, and the overall test tube holder train length may be adjusted to compensate for expansion/contraction of the holders due to environmental conditions.

5 Claims, 4 Drawing Figures

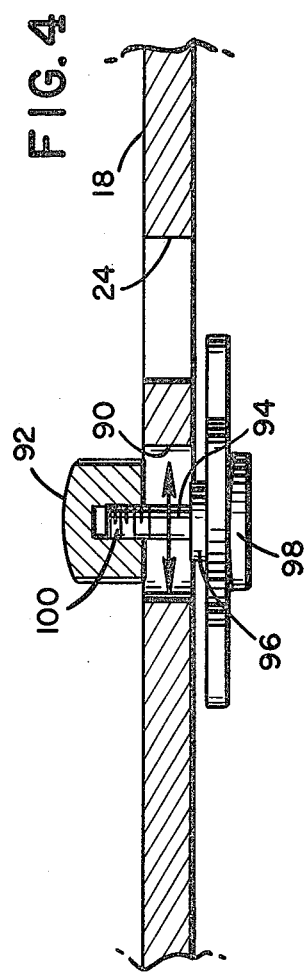
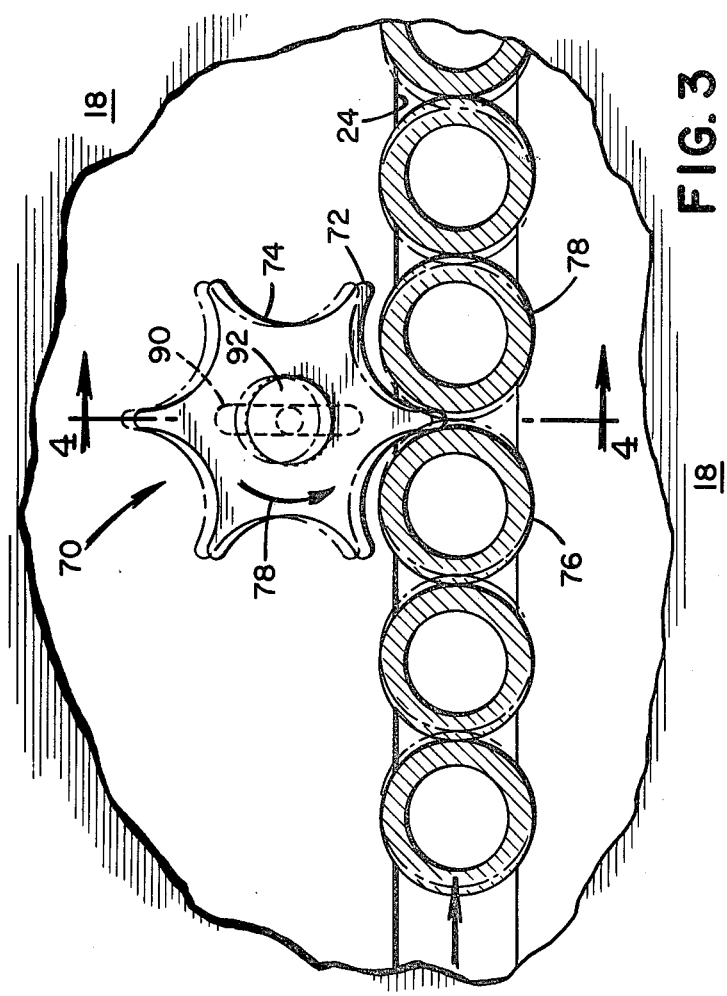
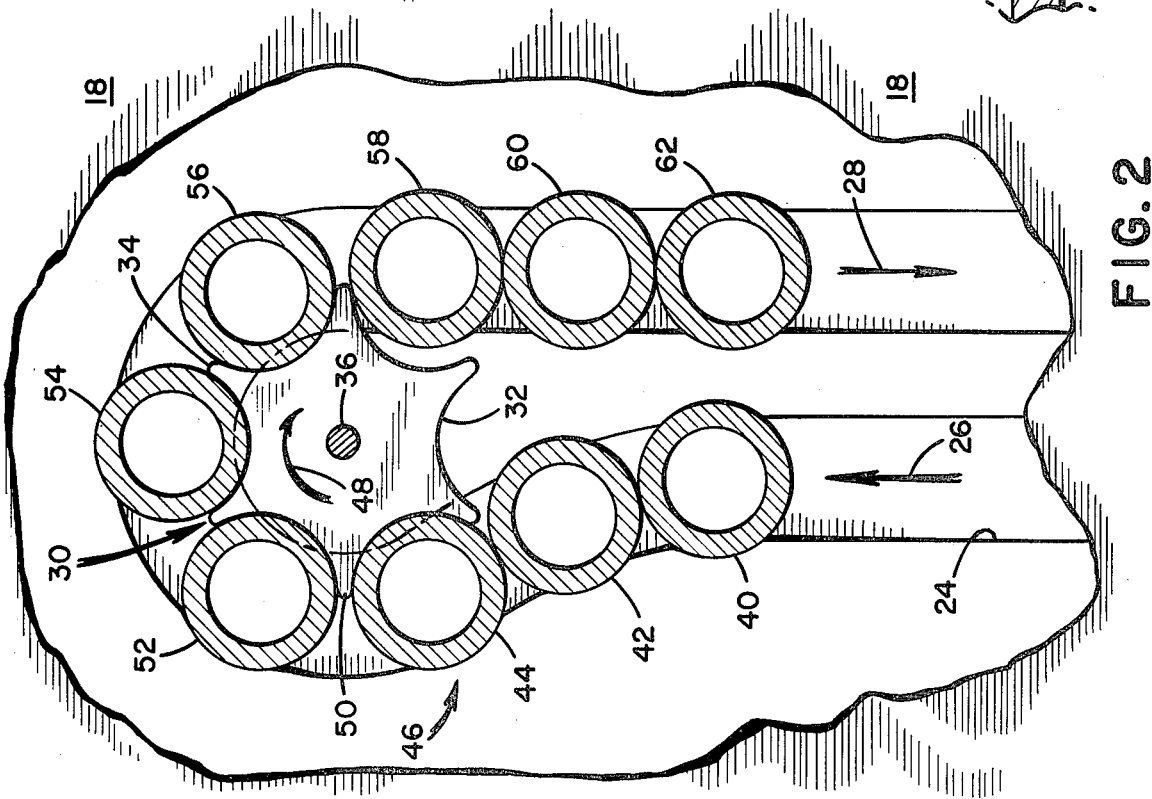

IDLER SPROCKETS FOR SAMPLE CHANGER TRACKS

BACKGROUND OF THE INVENTION

The present invention relates to improvements for use in automatic sample changers and more particularly, relates to apparatus for preventing excessive friction among test tube holders in a turn having a relatively short radius in the track of an automatic sample changer of the type used in the radiopharmaceutical field. The present invention also relates to means to adjust the relative spacing among the test tube holders in the continuous track of such automatic sample changer.

There have recently become available for use by the health professions, automatic systems for performing radiopharmaceutical tests, such as gamma counting. Such tests typically are based upon detecting and determining the level of radioactivity in a test tube. The level of radioactivity may be used in tests where radioactive antibodies are introduced into a laboratory sample, another operation such as washing the sample is performed, and then the amount of radiation remaining in the test tube is measured. Presently, such radioactive tests are used in the detection of hepatitis. It has been known to perform such tests manually, wherein the necessary preliminary operations are performed on a test tube and then the test tube is either irradiated or the radiation of the test tube is measured in a specially shielded location.

The automatic sample changer provides a system whereby the laboratory technician may load the samples into a number of test tubes and insert such test tubes into holders in a track in the machine and then leave the machine unattended to perform the desired test. Examples of such automatic sample changers may be seen in U.S. Pat. Nos. 4,024,395, issued May 17, 1977, and also in 4,001,584, issued Jan. 4, 1977. Automatic sample changers typically employ a plurality of plastic rings or pucks which are adapted to slide along a continuous track. The plastic rings or pucks are provided with a inside diameter which is chosen to accept a standard size test tube. The continuous track is arranged in a serpentine fashion and the test tube holder pucks are positively driven along the track by a driving wheel which contacts the rings. An elevator housing is located along the track such that each puck will pass into the housing. The test tube in that puck will be lowered into a shielded safe chamber and then a counting operation performed. The elevator then returns the test tube and puck to the track and the next succeeding sample is lowered by the elevator.

Needless to say, such automatic sample changers have provided a great improvement in the efficiency of the typical radioactive testing operation. Furthermore, although the original automatic sample changers employ up to 50 pucks or rings, i.e., it was possible to load 50 different radioactive samples into the automatic sample changer and then leave the machine unattended, more recent sample changers have been expanded and enlarged in successive steps to accept 100, 150, 200 and 300 separate and discrete samples in one machine top. As might be expected, the automatic sample changer which is able to accept 300 separate individual test tubes will necessarily require a long continuous track and a relatively large amount of surface area upon which to arrange the track. In order to overcome this requirement for a large surface area, an extremely complex and circuitous serpentine, track arrangement is provided in the top of the automatic sample changer so that the 300 test tube holders may be accomodated on a machine surface of reasonable size. However, in using such complex, circuitous, and convoluted track arrangement, it has been found that in attempting to drive the rings or pucks through particularly sharp turns, that large frictional forces are present between the individual pucks and also between the pucks and the continuous track. Such sharp turns may be likened to switchbacks used by railroads in traversing mountains.

Additionally, in systems utilizing a large quantity of plastic ring sample holders or pucks, it has been found upon relocating the system from one ambient temperature to another, that the rings will necessarily expand or contract. The cumulative effect of 300 rings undergoing such expansion or contraction will obviously affect the spacing between each puck and thereby affect the overall puck train length. The spacing is critical since, as mentioned above, the potential for a large amount of friction to be present between the puck and between the pucks and the track is particularly great when negotiating the many small radius turns along the continuous track.

SUMMARY OF THE INVENTION

The present invention provides a non-driven, free-wheeling tooth sprocket or star wheel rotatably mounted, in a first instance, at turns in the continuous track which have relatively small radii and, in a second instance, at any substantially straight portion of the continuous track. In the second instance, the sprocket is rotatably mounted and is also movable in a direction substantially perpendicular to the track, so as to adjust the extent of the engagement of the sprocket teeth with the plastic ring test tube holders, thereby adjusting the spacing between successive pucks. In the case where the free-wheeling sprocket or star wheel is mounted at a sharp turn or abrupt change of direction in the continuous track, the sprocket serves to prevent the pucks from binding in the track at the exit portion of the turn. This is accomplished by transferring the linear motion obtained from the moving pucks entering the turn, by causing the sprocket to rotate and linearly drive the pucks from the exit portion of the turn. Accordingly, a puck is never driven except in a relatively straight line since the sprocket prevents the puck train drive exerting forces on the pucks while they are in a turn, thereby avoiding excessive friction.

When using the idler positioner of the present invention in a substantially straight portion of the continuous track, the positioner is also star shaped and is provided with a predetermined number of fingers or teeth, and is also free-wheeling. The sprocket is mounted in a slot in the track plate so that the extent of penetration of the sprocket teeth into the gap between successive pucks may be adjusted. By moving the center of rotation of the idler wheel to varying distances from the center line of the continuous track, the idler sprocket is permitted to turn with the flow of the pucks yet to accurately control the individual puck spacing.

Accordingly, it is an object of the present invention to provide a means for permitting test tube holders to circumnavigate a close radius turn without excessive frictional forces.

It is another object of the present invention to provide such low friction, short radius turning capability by utilizing the linear motion of the plastic ring test tube holders at the entry into a turn and transferring this linear motion to the plastic rings at the exit portion of the turn.

It is a further object of the present invention to provide a suitable free-wheeling sprocket or star shaped idler wheel which can have a different number of teeth or points dependent upon the diameter of the test tube holders as well as the radius of the turn to be negotiated in the continuous track.

It is a still further object of the present invention to provide a free-wheeling star wheel which is useful in determining the spacing between the plastic ring test tube holders or pucks in the continuous puck train.

It is still a further object of the present invention to provide such free-wheeling tensioning starwheel with a slotted mounting arrangement which is manually adjustable such that the tensioner may be easily brought into and out of engagement with the continuous flow of the pucks in the track.

These and other objects of the present invention, as well as many of the attendant advantages thereof, will become more readily apparent when reference is made to the following description taken in conjunction with the accompanying drawings.

BRIEF DESCRIPTION OF THE DRAWINGS

FIG. 2 is a top plan view of the inventive idler drive wheel shown in position in a continuous track having a small diameter radius;

FIG. 3 is a top plan view of a portion of the top surface of the automatic sample changer of FIG. 1 wherein the idler positioner wheel of the present invention is shown in cooperation with test tube holder rings arranged in a linear portion of the continuous track; and FIG. 4 is a side elevation view of the inventive idler wheel of FIG. 3.

DETAILED DESCRIPTION OF THE PREFERRED EMBODIMENT

Figure 1:
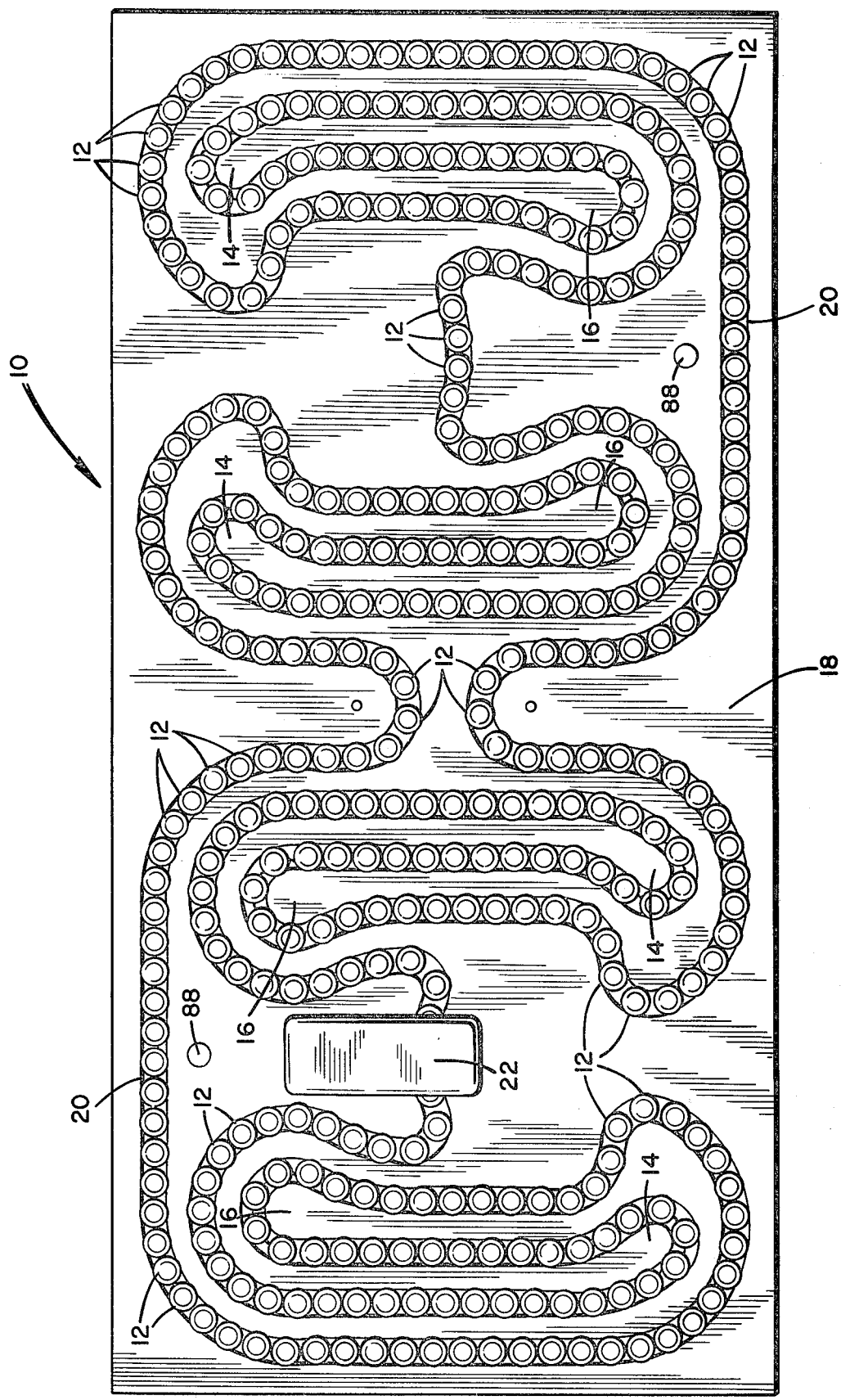
FIG. 1 is a top plan view of an automatic sample changer of the type having a large number of test tube holders or pucks arranged in a continuous track configuration having small radius turns.

FIG. 1 shows an automatic sample changer 10, as discussed above, which is capable of accepting three-hundred samples in three-hundred individual test tubes. The test tubes are inserted into the plastic rings or pucks, which are shown typically at 12. The plastic rings are then caused to circulate along a continuous track of a highly circuitous nature. Because it is necessary to provide the longest possible length of track within the smallest possible surface area, a relatively large number of small diameter bends or switchbacks will be required in the track. A bend of extremely small diameter is shown typically at 14 while a bend of somewhat larger diameter, but still of a problmatic nature, is shown at 16. The inventive idler wheel, or sprocket, provided by the present invention, is located at points at the center of the diameter of these turns, typically shown at 14 and 16. Such inventive sprocket wheel is, however, utilized beneath the top surface plate, or track plate, 18 of the automatic sample changer 10. A typical straight portion of the continuous track wherein the tensioning or spacing function provided by the present invention might be utilized is shown typically at 20.

In operation, the automatic sample changer employing the large number of rings in a continuous track advances or drives the rings in discrete steps such that upon entry into an elevator station 22, the test tube in the plastic ring will be lowered into the chamber of the machine and a test performed. Upon completion of the test, the test tube and ring are raised again and the ring is sent on its way along the continuous track and the next successive test tube is operated upon.

FIG. 2 shows the inventive drive helper or idler sprocket of the present invention, located in the portion of the track having a bend or switchback of small radius, which was shown typically at 14 in FIG. 1. The plastic rings or pucks are located in the track or open channel 24 and the direction of travel of the pucks is shown by arrows 26 and 28. The inventive idler sprocket 30 of the preferred embodiment is a starwheel or toothed wheel having large scalloped recesses between the teeth. The scalloped region 32 is generally of the same radius as the radius of the plastic rings or pucks which are used in the system. The sprocket 30 is provided with six teeth shown typically at 34 and which engage the moving plastic rings. The sprocket 30 is mounted on a shaft 36 such that the wheel is free to rotate, in other words, the inventive sprocket is an idler wheel.

In the preferred embodiment, the sprocket 30 is of a thickness to provide a rigid element. The number of teeth or points 34 on the sprocket 30, and the attendant scalloped areas 32, is based upon the radius of the turn in the continuous track. In the preferred embodiment shown in FIG. 2, the radius is such that 6 points are required on the inventive starwheel 30. However, in the event that the radius of the turn was greater than that shown in FIG. 2, i.e., one shown typically at 16 in FIG. 1, a lesser number of points would be required. Referring to the automatic sample changer of FIG. 1, the inventive starwheel in location 16 would require only 5 points.

In the operation of the preferred embodiment of FIG. 2, the sprocket 30 is mounted to freely rotate upon the axle or rotating shaft 36 and upon actuation of the drive means of the automatic sample changer, the following sequence will occur. The pucks 40, 42 and 44 are set in motion by being pushed one against the other, by the drive means of the sample changer. The pucks 40, 42 and 44 are thereby being driven into the turn of the relatively small radius. As may be seen, if driving and pushing of pucks 40, 42 and 44 were allowed to continue, there would be considerable binding of the pucks, one against the other, as well as against the track walls 24. However, by use of the present invention when puck 44 has reached the location shown generally at 46, puck 44 will contact the sprocket 30 and will begin to transfer the linear motion of the puck into rotary motion of the starwheel 30, in the direction of arrow 48. Moreover, as the sprocket 30 is driven into rotary motion, the sprocket teeth 34 will become inserted between the successive pucks such as the point 50, which has become inserted between pucks 44 and 52. Because the starwheel 30 is free-wheeling, i.e., is an idler element, the successive pucks being driven into contact with the sprocket teeth, such as puck 42 which is next in line, will drive the idler wheel and transfer the substantially linear motion of the puck 42 into rotary movement of the idler wheel 30. The linear motion, being in a relatively straight line, will necessarily involve the least amount of friction between the plastic rings and the continuous track 24. Additionally, the plastic rings which have been fed into the center of the turn, such as plastic ring 54, will be well separated from each other by the teeth 34 of the sprocket 30, and also will be driven through the turn not by the pushing action of the pucks one against the other, but rather by the rotary motion forces transferred to the sprocket 30. This rotary motion is ultimately transferred to the rings exiting the turn. Accordingly, pucks shown at 52, 54, and 56 may be said to float around the turn, since they are not being driven by pushing against one another but rather merely being urged along by the starwheel.

The additional advantage provided by the present invention is evidenced by the manner in which pucks 58, 60 and 62 are exited from the turn with a substantially linear force. This linear force is provided by the transfer of the rotary movement from the sprocket 30. Accordingly, the energy required by the system drive means to drive the plastic rings along the continuous track is determined only by the requirement for movement in a relatively straight line since the sharp bends 14 or 16 in FIG. 1, offer no direct resistance to the puck drive means.

FIG. 3 shows the inventive idler drive wheel of the present invention utilized as a ring positioner or slack tensioner in the automatic sample changer machine 10 of FIG. 1. In the preferred embodiment, the idler tension wheel assembly 70 is mounted beneath the track plate 18 of FIG. 1. The problem which is solved by the use of the inventive positioner 70 is, as mentioned above, related to the fact that the overall combined length of the plastic rings or pucks is a function of the ambient temperature and humidity. When abrupt or excessive temperature and humidity changes occur, the rings may swell or shrink, thereby jamming in the track, either due to the lack of space between each ring or the excessive space between the rings, which will cause binding in the turns. Utilization of the sprocket shown in FIG. 3 will aid in relieving binding in the turn.

Accordingly, as in FIG. 2, the positioner 70 is mounted beneath the track plate 18 a portion of which is shown removed in FIG. 3 so that the inventive positioner sprocket 70 may be seen. The manner of mounting the sprocket 70 will be shown in more detail in FIG. 4. However, in FIG. 3, it may be seen that the plastic rings, as they move along the continuous track 24, will contact the teeth 72 of the sprocket 70 and the rings will fit into the scalloped portions of the sprocket 70, shown typically at 74.

The sprocket 70 is freely mounted as an idler, i.e., it is not provided with an independent drive means. Accordingly, upon contact of the starwheel 70 by a plastic ring, such as the ring shown at 76, motion will be imparted to the wheel positioner 70 in the direction of arrow 78. By inserting the tooth 72 of the wheel 70 between successive pucks, such as 76 and 78, it may be seen that an amount of space is taken up in the overall length of the puck train equal to the width of the point 72. However, more importantly, is the ability of the present invention to vary the amount of penetration of the finger into the interstices which occur between successive pucks. The variable positioning capability of the present invention is made possible in part by the taper of the teeth 72 and by a slot 90 in the track plate 18. The slot 90 is shown in phantom and located beneath the sprocket 70. Once a position is selected for the sprocket 70, it may be secured by rotating a thumb screw or knurled knob 92. The interaction of the knurled knob 92 and the slot 90 will be discussed in more detail in relation to FIG. 4.

FIG. 4 is a cross section of the positioning sprocket of the present invention taken along section 4-4. In this cross section, the knurled knob 92 is located above the track plate 18. A threaded rod 94 having a shoulder portion 96 and a hub 98 is provided to cooperate with the knurled knob 92. The hub 98 is formed with a diameter greater than the axial bore of the inventive idler sprocket 70, while the shoulder portion 96 is of a diameter less than the axial bore through the center of the inventive sprocket 70. However, the shoulder portion is greater than the width of the slot 90 which has been milled into the track plate 18. A threaded portion 100 is provided at the end of the shaft portion 94 which protrudes through the slot 90. The shaft 94 is of a diameter which is less than the width of the slot 90.

In operation, the location for the inventive sprocket 70 is chosen in relation to the desired amount of penetration of the sprocket finger 72 into the interstices of the puck train, and upon rotating the knurled knob 92, the shoulder portion 96 is drawn up against the track plate 18 and secured thereto. However, since the shoulder portion 96 is of a smaller diameter than the axial bore in the sprocket, the inventive sprocket 70 is permitted to freely spin. In this manner, the length of the puck train may be controlled regardless of changes in temperature or humidity in the environment of the automatic sample changer.

It is understood, of course, that the foregoing description is given by way of example only, and that various other means may be utilized to embody the teaching of the present invention. For example, the sprocket wheel may have 5 or 6 or 7 teeth or arms and the specific locking apparatus using the threaded shouldered rod may be replaced by various other locking means.

What is claimed is:

1. Apparatus for use in an automatic sample changer employing a plurality of rings for receiving test tubes wherein the rings are arranged to be driven along a curved track having at least one substantially straight portion, the apparatus comprising:

sprocket means mounted in the center of curvature of at least one small-radius turn on said track said sprocket means being formed having well defined, tapered teeth wherein the space between said teeth is arcuately shaped having a radius substantially equal to the radius of said rings;

means for rotatably mounting said sprocket means inside the arc of said small-radius turn at a location to contact the driven rings entering said turn and to transfer the force of said driven rings to the rings exiting said turn;

a second toothed sprocket wheel movably mounted for free rotation in an elongated slot in the apparatus adjacent the straight portion of the track;

a rod attached to the center of said second toothed sprocket wheel and extending through said slot; and means cooperating with said rod for securing said toothed sprocket at any predetermined location along said slot such that said driven rings rotate said second sprocket and the teeth of the sprocket penetrate the space between successive rings based upon said predetermined location, whereby the extent of penetration of said teeth of said second sprocket wheel determines the spacing of said rings.

2. The apparatus of claim 1 wherein said sprocket means has six teeth.

3. The apparatus of claim 1 wherein said sprocket means has five teeth.

4. In a mechanism having a plurality of abutting rings driven along a continuous track of an automatic sample changer by having a pushing force imparted to at least one of said rings and being subsequently imparted to all of said rings, one to another, wherein the continuous track has at least one change of direction formed by a bend of small radius and at least one substantially straight portion, the improvement comprising:
- a toothed sprocket wheel having well-defined tapered teeth with a scalloped recess between adjacent teeth and being mounted for free axial rotation and disposed in proximity to said bend in said track such that each successive driven ring contacts a tooth of said sprocket and is moved into one of said recesses as said ring enters said bend and rotating said sprocket wheel, said teeth thereby being interposed between successive rings such that said rings are not abutting each other thereby causing said sprocket wheel to impart rotary motion to said rings in said bend and linear motion to said rings exiting said bend;
- a second toothed sprocket wheel movably mounted for free rotation in an elongated slot in the mechanism adjacent the straight portion of the track;
- a rod attached to the center of said second toothed sprocket wheel and extending through said slot; and
- means cooperating with said rod for securing said second toothed sprocket at any predetermined location along said slot such that said driven rings rotate said second sprocket and the teeth of the sprocket penetrate the space between successive rings based upon said predetermined location, whereby the extent of penetration of said teeth of said second sprocket wheel determines the spacing of said rings.

5. Apparatus for use on an automatic sample changer having a continuous track and a plurality of test tube rings driven along the track comprising:
- a freely rotating sprocket wheel mounted in an elongated slot adjacent the track and having a rod attached to said sprocket wheel and extending through said slot and a means which cooperates with said rod for securing the sprocket at any location along said slot such that the extent of penetration of the sprocket teeth into the plurality of rings may be adjusted by securing said sprocket wheel at a predetermined location along said slot, such that said teeth are interposed between adjacent rings thereby providing a space between adjacent rings in contact with said sprocket teeth.

* * * * *